US005922551A

United States Patent [19]
Durbin et al.

[11] Patent Number: 5,922,551
[45] Date of Patent: Jul. 13, 1999

[54] AGGLUTRIMETRIC PLATELET BINDING ASSAYS IN BLOOD

[75] Inventors: Dennis A. Durbin, Solana Beach; Theodore T. Lee, Santa Fe; Boris I. Ratnikov, San Diego; Robert S. Hillman, San Diego; Jeffrey W. Smith, San Diego, all of Calif.

[73] Assignee: Accumetrics, Inc., San Diego, Calif.

[21] Appl. No.: 08/820,999

[22] Filed: Mar. 20, 1997

Related U.S. Application Data

[51] Int. Cl.$^6$ .................. G01N 33/546; G01N 33/557
[52] U.S. Cl. ................. 435/7.21; 435/7.8; 435/13; 436/518; 436/523; 436/524; 436/534; 436/69; 436/164
[58] Field of Search .................. 435/7.21, 7.8, 435/13, 975; 436/503, 518, 524, 528, 533, 534, 10, 69, 164, 523

[56] References Cited

U.S. PATENT DOCUMENTS

| | | |
|---|---|---|
| 4,224,304 | 9/1980 | Sawai et al. . |
| 4,760,030 | 7/1988 | Peterson et al. .................. 436/509 |
| 4,793,180 | 12/1988 | Stewart et al. ..................... 73/335 |
| 5,004,923 | 4/1991 | Hillman et al. . |
| 5,110,727 | 5/1992 | Oberhardt ........................ 435/13 |
| 5,202,269 | 4/1993 | Ito et al. .......................... 436/533 |
| 5,246,832 | 9/1993 | Michelson et al. ................ 435/7.2 |
| 5,252,459 | 10/1993 | Tarcha et al. ..................... 435/6 |
| 5,252,496 | 10/1993 | Kang et al. ...................... 436/529 |
| 5,284,751 | 2/1994 | Frelinger, III et al. ............. 435/7.21 |
| 5,422,239 | 6/1995 | Wands et al. .................... 435/7.94 |
| 5,427,913 | 6/1995 | Shaw et al. ..................... 435/7.21 |
| 5,455,228 | 10/1995 | Coller et al. ..................... 514/17 |
| 5,470,738 | 11/1995 | Frelinger, III et al. ............ 435/240.27 |
| 5,529,901 | 6/1996 | Van Doorn et al. ............... 435/6 |
| 5,763,189 | 6/1998 | Buechler et al. ................. 435/7.1 |
| 5,763,199 | 6/1998 | Coller ............................ 435/7.21 |

FOREIGN PATENT DOCUMENTS

96/10749  4/1996  WIPO .

OTHER PUBLICATIONS

Brochure for "Maximum Humidity Indicators," Model Nos. MXC56789 and MX56789, Humidial Corporation: Colton, CA, pp. 1–3 (Oct. 1996).

Coller, "Blockade of Platelet GPllb/llIa Receptors as an Antithrombotic Strategy," *Circulation*, 92(9):2373–2380 (1995).

Fabian, "Near–Infrared Absorbing Dyes," *Chem. Rev.*, 92:1197–1226 (1992).

Patonay and Antoine, "Near–Infrared Fluorogenic Labels: New Approach to an Old Problem," *Analytical Chemistry*, 63(6):321A–327A (1991).

Kouns et al., "A Conformation–Dependent Epitope of Human Platelet Glycoprotein IIIa," *The Journal of Biological Chemistry*, 265(33):20594–20601 (1990).

Smith et al., "Protein Loop Grafting to Construct a Variant of Tissue–Type Plasminogen Activator that Binds Platelet Integrin $\alpha_{IIb}\beta_3$," *The Journal of Biological Chemistry*, 270(51):30486–30490 (1995).

Coller et al., "A Rapid, Whole Blood, Bedside Assay to Monitor Platelet Glycoprotein (GP) IIb/IIIa Blockade, "*Blood*, 84(10)(abstract 1883):4/4a (1994).

Coller, 1980. Interaction of normal, thrombasthenic, and Bernard–Soulier platelets with immobilized fibrinogen: defective platelet–fibrinogen interaction in thrombasthenia. Blood 55(2): 169–178.

Coller et al., 1983. A murine monoclonal antibody that completely blocks the binding of fibrinogen to platelets produces a thrombasthenic–like state in normal platelets and binds to glycoproteins IIb and/or IIIa. J. Clin. Investigation 72:325–338.

Coller et al., Feb. 1997. Rapid and simple platelet function assay to assess glycoprotein IIb/IIIa receptor blockade. Circulation 95(4):860–867.

Retzinger et al., 1991. Quantitation of plasma factor XIIIa activity using fibrin–coated microscopic latex beads. Analytical Biochemistry 195:18–23.

*Primary Examiner*—James C. Housel
*Assistant Examiner*—James L. Grun
*Attorney, Agent, or Firm*—Bertram I. Rowland; Flehr Hohbach Test Albritton and Herbert LLP

[57] ABSTRACT

Methodology which avoids the problems associated with interference from whole blood is provided for instrumented determination of platelet binding function. Particularly, small particles to which fibrinogen is bound, and which contain an infrared light absorbing dye, are used to determine the binding of platelets in a whole blood sample to the fibrinogen. Agglutination of the platelets with the coated particles is determined by a change in infrared light absorption characteristics.

7 Claims, 4 Drawing Sheets

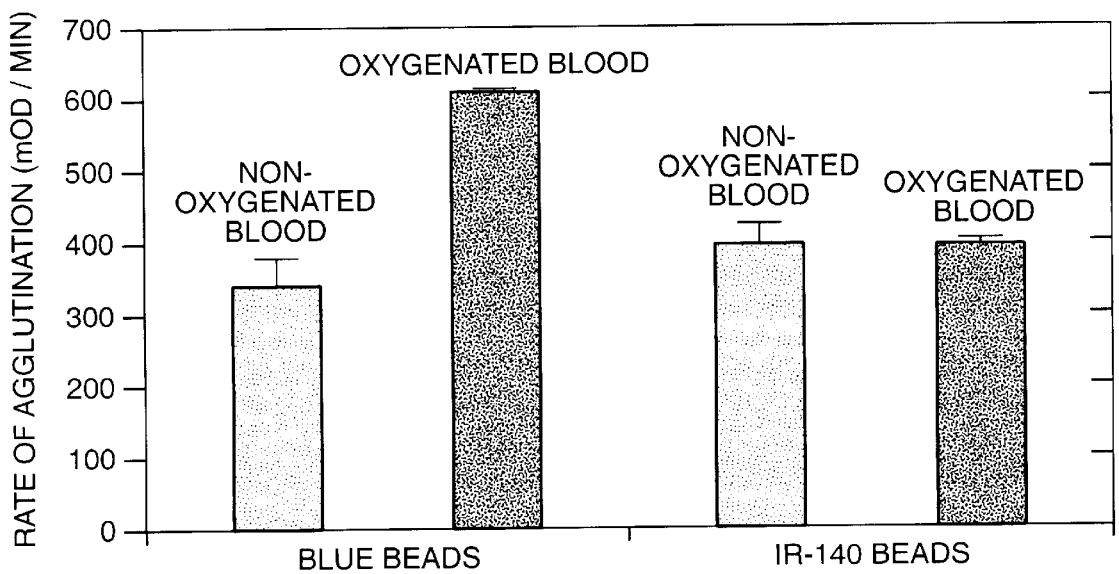
FIG._1
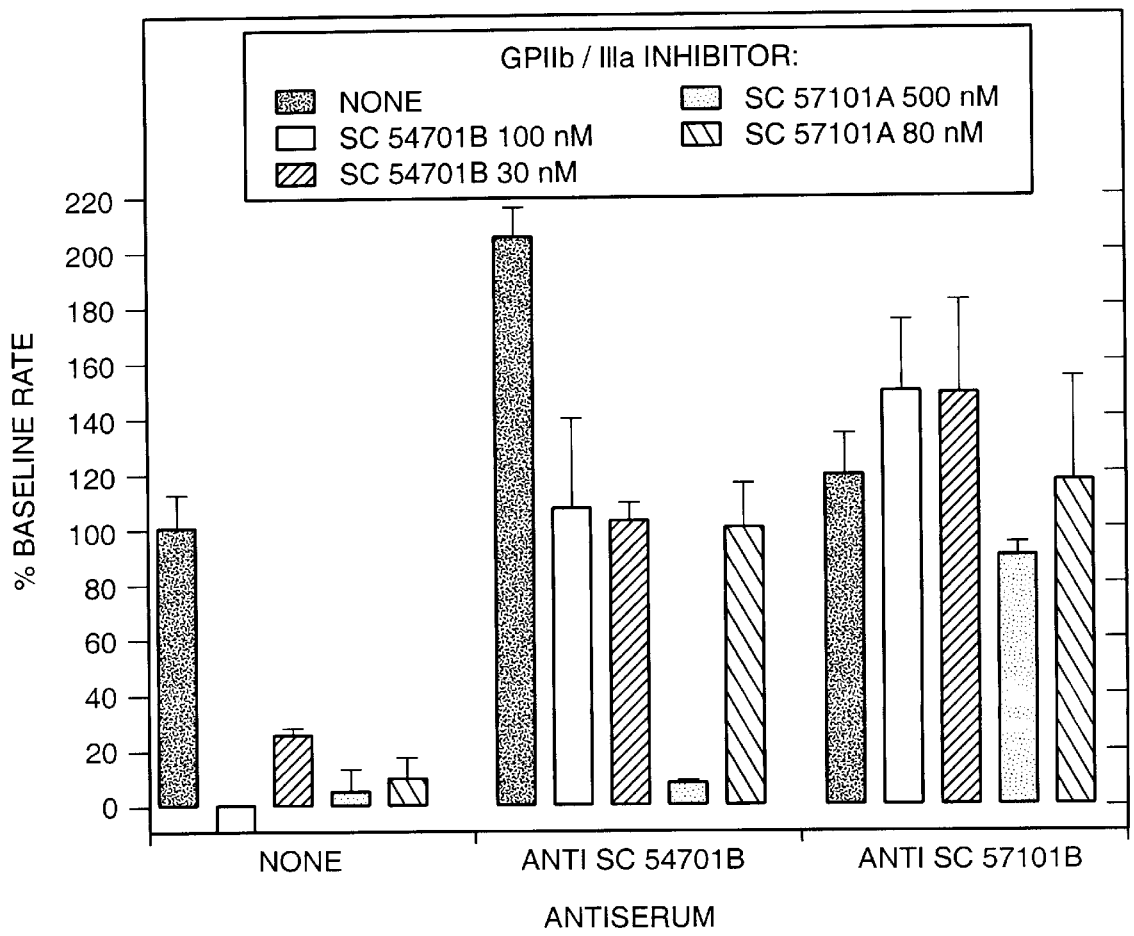
FIG._5

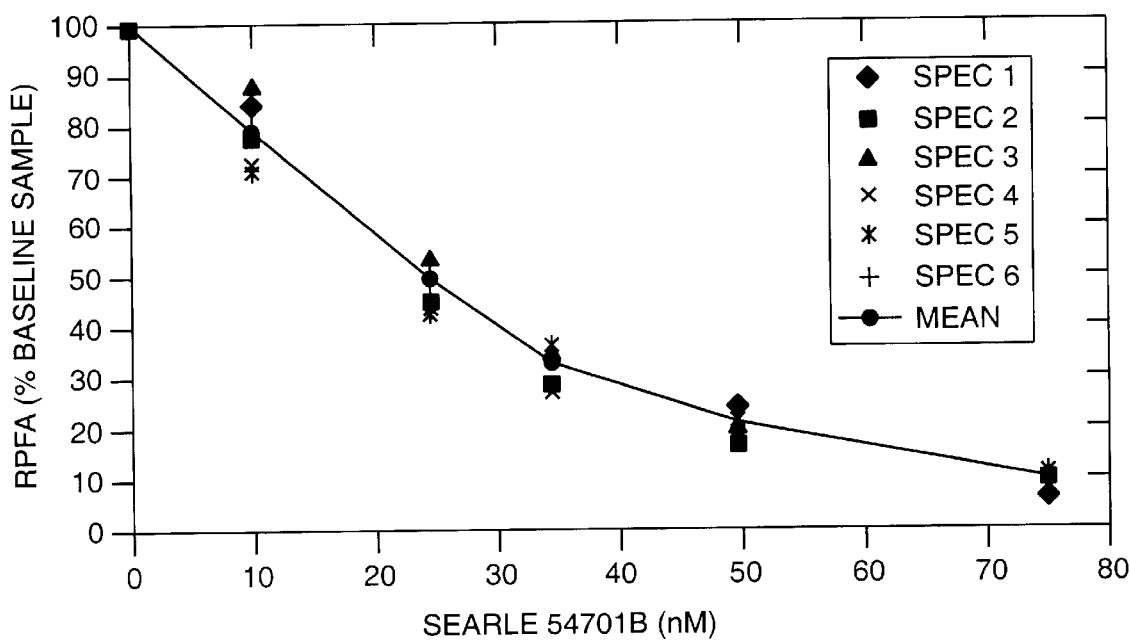
FIG._2
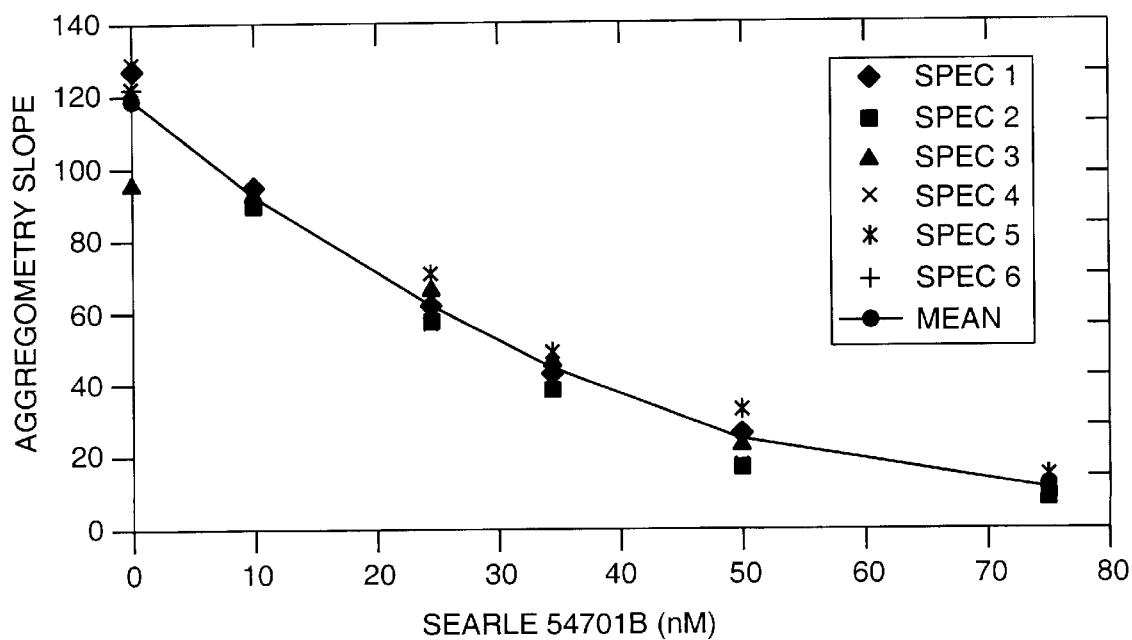
FIG._3

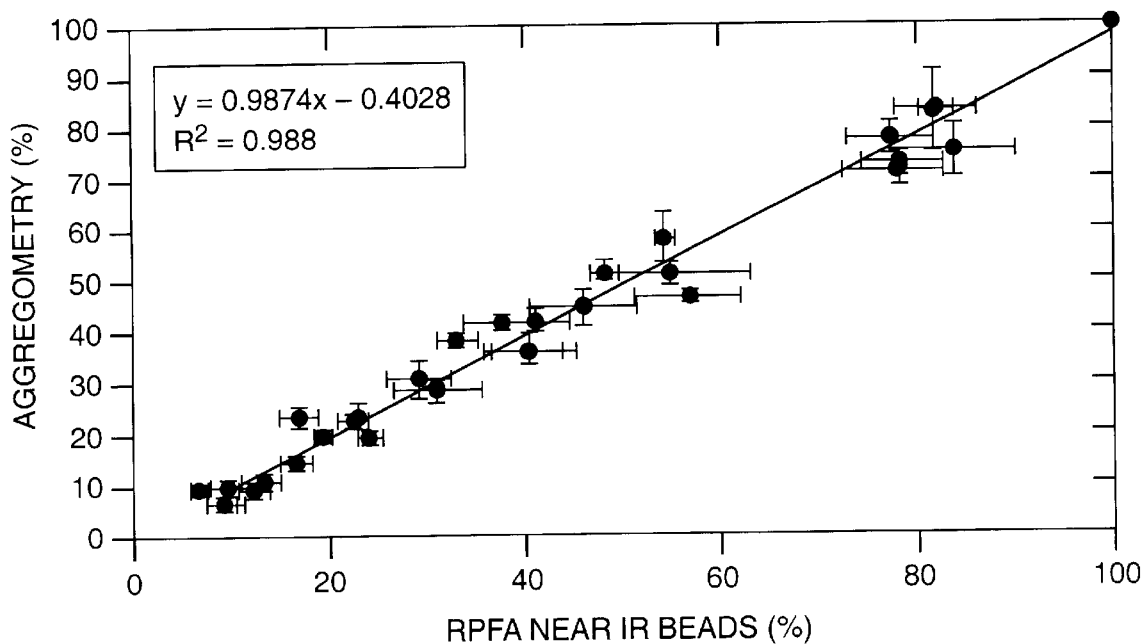
FIG._4A
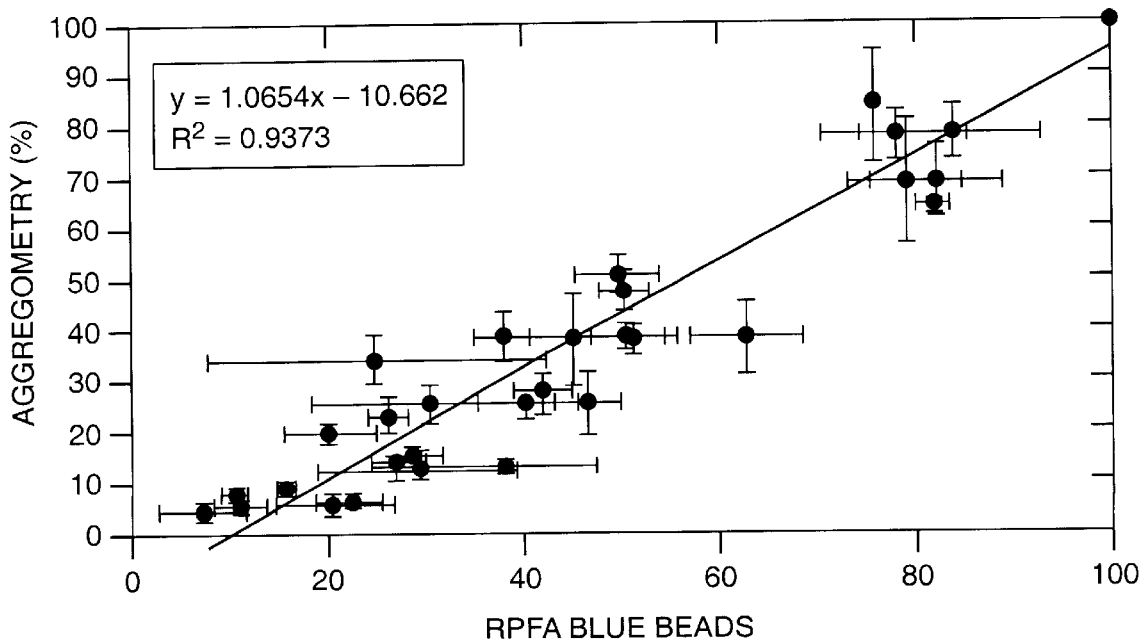
FIG._4B

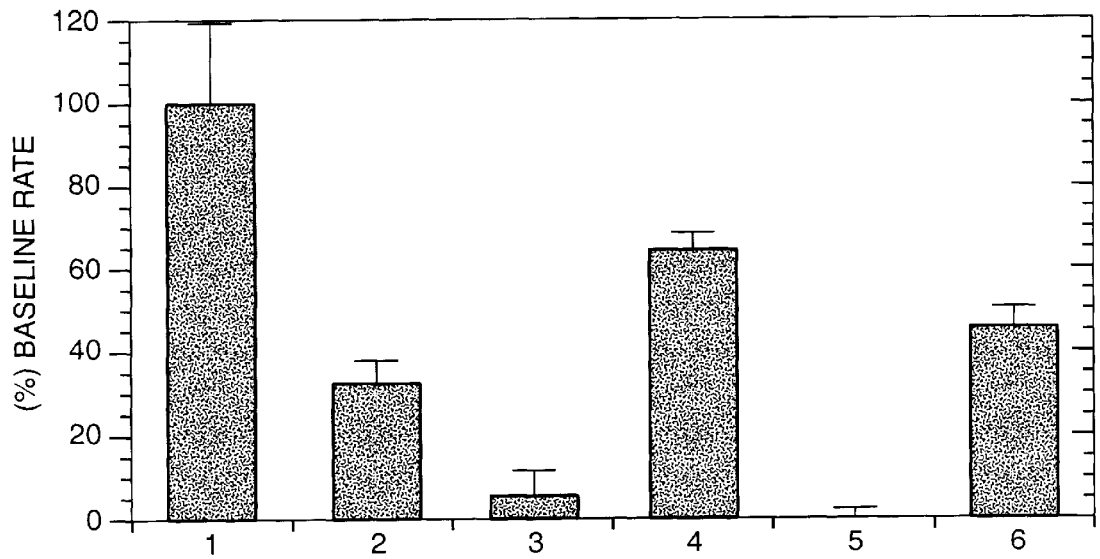
FIG._6
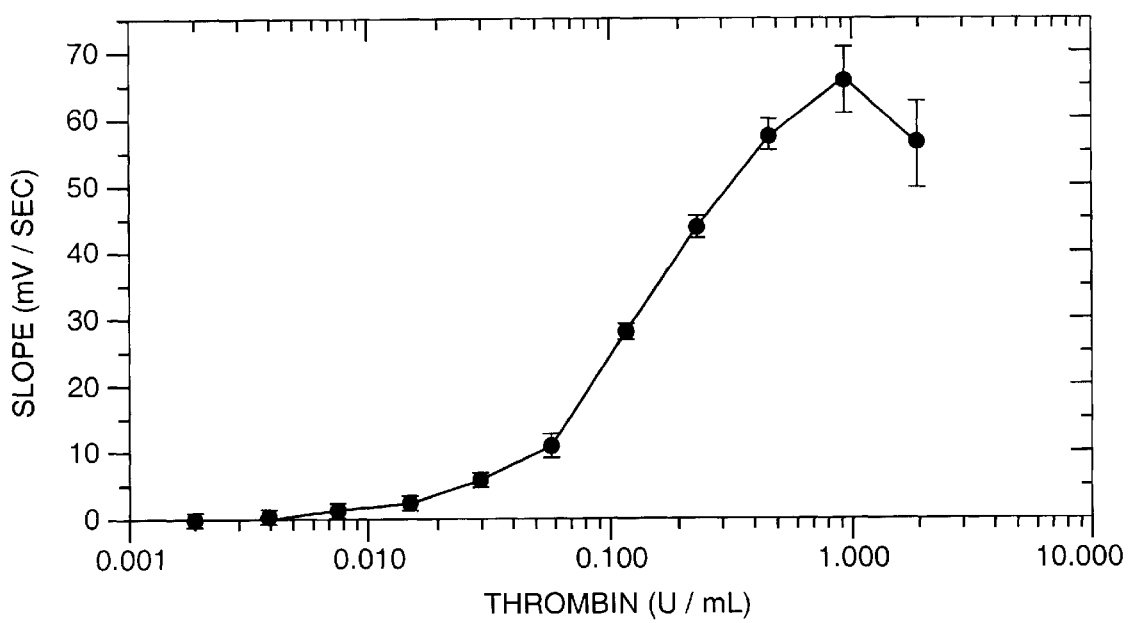
FIG._7

AGGLUTRIMETRIC PLATELET BINDING ASSAYS IN BLOOD

INTRODUCTION

BACKGROUND

The medical industry has become increasingly dependent upon the ability to measure various entities in physiological fluids in order to be able to determine the health status of an individual, dosage level for drugs, use of illegal drugs, genomic sequences, and the like. Thus, the capability of taking a physiological sample and rapidly analyzing for a particular component has made medical therapies more efficient and increasingly successful.

In many instances, one wishes to use blood as a source to diagnose a patients health or to monitor the efficacy of drugs that have been administered to the patient. Blood as a source for the determination of these parameters has many deficiencies. Among its deficiencies when used directly or even when diluted with buffer are: blood rapidly coagulates, blood contains a large number of light absorbing and florescent substances; blood exhibits variations in composition, its characteristics can change in relation to the reagents used in the assays; and blood exhibits variations in the presence or absence of oxygen. These properties complicate the use of blood as a sample for diagnostic purposes. Various techniques have been employed to avoid these problems; high dilution, addition of anticoagulants, separation of blood into plasma and its cellular components, and the like. During such manipulations, great care must be taken to avoid lysis of red blood cells to avoid the release of hemoglobin, which can interfere with diagnostic assays. Despite the problems associated with the use of blood as the sample medium, in many instances, blood is the only source which provides the information of interest. Therefore, identifying ways of using whole blood, while diminishing the interference from its constituents is highly desirable.

There is, therefore, substantial interest in devising new approaches for using and manipulating blood for diagnostic purposes. One area of particular interest is the assessment of platelet function. The role of platelets in mammalian physiology is extraordinarily diverse, but their primary role is in promoting thrombus formation. In many situations, one wishes to evaluate the ability of the blood to clot, a parameter that is frequently controlled by the ability of platelets to adhere and/or aggregate. Thus, one may wish to assess the adhesive functions of platelets. For example, one may wish to know whether to administer drugs that will block, or promote, clot formation, or one may need to detect deficiencies in platelet function prior to surgical procedures. In other instances one may be interested in evaluating the effectiveness of a platelet inhibitor that is being tested, as a new drug, or is being used as approved clinical treatment in a patient.

Relevant Literature

U.S. Pat. No. 5,455,228 and PCT application Ser. No. WO96/10749 describe a peptide resistant ligand and a platelet blockade assay, respectively. See also, Coller, B. S. Platelets in cardiovascular thrombosis and thrombolysis. In: Fozzard, et al. eds. *The Heart and Cardiovascular System*, 2nd ed. New York, N.Y.: Raven Press; 1992:219–273. For a description of infrared absorbing dyes, see Fabian et al., Chem. Rev. 1992, 92, 1196–1226.

Other techniques which have been taught for determining platelets and/or platelet function include: PCT applications WO94/12664; WO94/22018; WO92/08982; WO89/00200; U.S. Pat. Nos. 5,427,913; 5,306,632; 5,523,238; 5,266,462; 5,246, 832; 5,114,842; and EPA 0 165 68. Articles of interest include: Beer et al., Immobilized Arg-Gly-Asp (RGD) peptides of varying lengths as structural probes of the platelet glycoprotein IIbIIIa receptor. Blood 79, 117–128. 1992. Coller et al., Collagen-platelet interactions: Evidence for a direct interaction of collagen with platelet GPIa/IIa and an indirect interaction with platelet GPIIb-IIIa mediated by adhesive proteins. Blood 74, 182–192, 1989; Coller et al., Studies of activated GPIIb-IIIa receptors on the luminal surface of adherent platelets. J. Clin Invest. 92, 2796–2806, 1993; and Pfueller et al., Role of plasma proteins in the interaction of human platelets with particles. Thrombosis Research 12, 979–990, 1978.

SUMMARY OF THE INVENTION

An agglutimetric assay is described which employs particles that absorb light in the infrared region. Aggregation of particles is detected by changes in infrared absorption of the sample media. The assay may be used to determine the presence of a component of interest, the function of that component, or determine the amount of the component. The methodology permits the use of whole blood or slightly diluted blood, rather than plasma. The method involves mixing the particle reagent, any additional reagents as appropriate, and the sample. Then, the change in infrared light absorption of the medium is measured. The result may be compared to controls for quantitative determination.

BRIEF DESCRIPTION OF THE DRAWINGS

FIG. 1 is a graph depicting them effect of oxygenation of blood on the baseline rates obtained with particles that absorb in the visible range, or in the near infrared range. Because the oxygenation of blood changes the hemoglobin absorption profile, which alters the absorbance of the blood in the visible range, there is significant interference with the assay. Hence, with blue beads oxygenation of blood causes an artifactual increase in the observed rates of agglutination. In contrast, using particles which absorb light in the IR range, oxygenation of blood has no effect. Hence the rates that are reported are independent of the oxygenation of the blood.

FIG. 2 is a graph of the results of a rapid platelet function assay (RPFA) of Searle compound 54701B. The RPFA was performed and maximum activity determined as described in the Experimental Section. The mean and individual results from six separate donors is shown in this and the subsequent figure.

FIG. 3 is a graph of the results of the optical platelet aggregation assay of Searle compound 54701B using 20 $\mu$M ADP agonist. Optical platelet aggregation was performed as described in the Experimental Section. Results shown are the maximum slope data (% change of aggregation/minute) and are not normalized values.

FIGS. 4A–4B are graphs comparing the results of platelet aggregation obtained using a commercially available system (platelet aggregometry) plotted against platelet activity obtained with RPFA. Two panels are shown, each depicts the RPFA performed with a different set of dyed particles. In FIG. 4A, the particles absorb in the near IR range. In FIG. 4B, the particles absorb in the visible range. The data in FIG. 4A are the mean and standard error obtained from dose reponse curve values performed on six subjects for three days. The correlation coefficient is 0.99 and there is minimal bias (0.4%) The data in FIG, 4B are from an experiment performed in the same manner using beads dyed with a blue dye. The correlation coefficient is 0.94 and there is a significant bias present (10.7%).

FIG. 5 is a graph, showing neutralization of GPIIb/IIIa inhibitory compounds, Searle Compound 54701B and Searle Compound 57101A, by rabbit antisera raised against those compounds. Results shown are the normalized slope data (% baseline rate when no drug and no antisera were added).

FIG. 6 is a graph, showing reversal of GPIIb/IIIa inhibition by Gel Filtration of blood samples, treated with GPIIb/IIIa inhibitors. Results shown are normalized slope data (% baseline rate of untreated blood sample). X axis legend: 1—untreated blood, 2—untreated blood after gel filtration, 3—blood treated with 100 nM Searle Compound 54701B, 4—blood treated with 100 nM Searle Compound 54701B after gel filtration, 5—blood treated with 500 nM Searle Compound 57101B, 6—blood treated with 500 nM Searle Compound 57101B after gel filtration.

FIG. 7 is a graph showing a Thrombin Induced Agglutination dose response curve. A 160 ul aliquot of mixture containing a known concentration of thrombin in a light-scattering medium (1% solids suspension of 0.5 um polystyrene microspheres in 10 mM HEPES 150 mM NaCl, 2 mg/ml BSA 0.05% Tween 20) to mimic light scattering characteristics of whole blood, was added to a plastic cuvette containing iso-TRAP and microparticles. The mechanical mixing cycle was activated for 1 minute with optical reading sampled at a rate of 16 per second. Microagglutination was determined by the rate of change of the optical density of the solution over at fixed interval. The data are reported as the slope of thrombin-induced agglutination in mV/sec vs. the concentration of thrombin in the assay.

DESCRIPTION OF SPECIFIC EMBODIMENTS

In accordance with the subject invention, the character of a sample is determined by combining the sample with particles which absorb in the infrared, where the rate and/or extent of aggregation of the particles is modulated by the character of the sample. Normally, the character of the sample will be associated with the presence and amount of a component of interest. In other situations the character may be associated with the activity of the sample in relation to its effect on an event, e.g. clotting. Other reagents may also be present, depending upon the nature of the component and the protocol of the assay. After sufficient time for any aggregation to occur, the assay mixture is illuminated with infrared light and the change in absorption determined. The value obtained may be compared to a standard for a quantitative determination of the amount of component in the sample.

The method is flexible and can be used to assess several parameters, including the presence of a component in the sample, the character of the sample, or even the combined effect of several components in the sample on the penultimate agglutimetric reaction. However, for the purposes of the description, the description will refer to the component of interest and its functional activity, rather than the character of the sample.

Any sample can be used. The method is particularly advantageous for those samples which contain entities which might interfere with spectrophotometric determination at wavelengths other than infrared. The sample may be any physiological fluid, environmental fluid, processing fluid, effluent or influx. The subject methodology finds immediate application with physiological fluids, more particularly blood or plasma. By using the subject methodology, less care in preparing the plasma is required, since released hemoglobin and other metal or non-metal porphyrins will have reduced interference in the methodology.

Particular samples may include, as indicated, blood, plasma, cerebrospinal fluid, saliva, urine, and the like, more particularly, those samples which have an interfering substance which absorbs or emits light in the range of about 300 nm to about 700 nm. Therefore, the subject methodology finds use, particularly with whole blood, by employing infrared light, where the signal from the sample is not significantly affected by the variations in absorption resulting from changes in oxygenation of the sample.

The sample may be subject to pre-treatment, depending upon the nature of the sample. Generally, the sample may be used without significant sample manipulation preparation. However, preparation may include dilution, concentration, extraction, chromatography, electrophoresis, and the like. Desirably, there will be minimum sample preparation. In accordance with the subject invention, whole blood may be used, which is diluted less than about 10-fold, usually diluted less than about 5-fold, preferably less than about 1-fold, and, more preferably less than about 0.5-fold. The blood will be modified to prevent coagulation, by using various anti-coagulants. Anti-coagulants include citrate, heparin, thrombin inhibitors, and the like. Conveniently, citrate is employed in a small volume in relation to the volume of the whole blood sample, generally less than about 25% v/v, usually less than about 10% v/v, and may be less than about 1% v/v.

Any compound of interest can be employed which may serve to inhibit or enhance the aggregation of the particles. Thus, the component of interest may be any compound which interacts, either directly or indirectly, with a compound on the surface of the particles, so as to enhance or inhibit aggregation, where indirectly intends that the compound of interest reacts directly or indirectly with a reagent which serves to enhance or inhibit aggregation. For indirect reaction, one may consider enzyme inhibitors. For example, a thrombin inhibitor would react with the thrombin to inhibit the reaction of thrombin with fibrinogen. Where the particles are coated with fibrinogen, the inhibitor would reduce the amount of aggregation by reducing the extent of reaction of the thrombin with the fibrinogen on the particles. Inhibitors of other blood factors which ultimately affect the transformation of fibrinogen to fibrin would act similarly in an indirect manner.

Thus, the components of interest may be small molecules, generally from about 100–5000 Dal, more usually from about 100–2000 Dal, such as synthetic drugs, biocides, e.g. pesticides, herbicides, etc., antibiotics, naturally occurring ligands or fragments of naturally occurring compounds, amino acids, saccharides, lipids, nucleosides and nucleotides, and their oligomers, particularly oligopeptides, oligosaccharides or oligonucleotides, and combinations thereof.

Illustrative compounds include drugs of abuse, such as tetrahydrocannabinol, morphine, heroin, cocaine, and methamphetamine, barbiturates, tranquilizers and antidepressants, e.g. librium, diazepams, and tricyclics, diphenylhydantoin, immunosuppressants, e.g. cyclosporine and FK506, cardiovascular drugs, e.g. digitonin, nitroglycerin, etc., clotting inhibitors, e.g. Warfarin, heparin, low molecular weight heparin, aggregation activators, e.g iso-TRAP, analgesics, anaesthetics, antihypertensive reagents, e.g. renin inhibitors, lipid A, toxins, IIb-IIIa antagonists including compounds such as RGD and KGD-based peptidomimetics, one subset of these compounds includes Searle compound 54701, Searle compound 57101, ReoPro (Centacor), Integrilin (Cor), Roche Ro440-3888, Hoechst S 1197, Merck L-738,167, TAK 029 (Tap Holdings), Boehringer Ingelheim BIBU 52ZW.

The compounds may be macromolecular compounds, which will have a molecular weight of at least about 5 kD, more usually at least 10 kD, and generally less than about 1 million kD, more usually less than about 600,000 kD. These compounds may include various natural or synthetic polymers, such as polypeptides, nucleic acids, polysaccharides, lignins, polylipids, combinations, such as mucopolysaccharides, glycoproteins, sulfonated polysaccharides, lipopolysaccharides, and the like.

Illustrative macromolecular compounds include insulin, blood factors, e.g. Factor V, VI, VII, VIIIc, VIII vw, IX, X, X, XI and XII, soluble histocompatibility antigens, e.g. sHLA, β-amyloid, HIV gp120 and p41, CD3, CD28, B7, glutamic acid dehydrogenase, tissue plasminogen activator, colony stimulating factors: G, M, and GM, perforins, complement proteins, bacterial and fungal proteins, protista proteins, viral proteins).

Finally, the component of interest may be a combination of one or more different categories of compounds, such as viruses, organelles, such as mitochondria, prokaryotes and eukaryotes, such as bacteria, fungi, protista, chlamydia, mammalian cells, such as platelets, cancer cells, e.g. leukemia and lymphoma, and the like. Viruses of interest include HIV, HTLV, papilloma virus, herpes virus, hepatitis viruses, adenoviruses, rhinoviruses, and the like.

The particles which are employed will generally be smaller than about $50\mu$, more usually smaller than about $25\mu$, usually being at least about $0.1\mu$, preferably from about $1–10\mu$, more preferably from about $2–8\mu$. The composition of the particle may be any convenient composition, such as bioglas, organic polymers, e.g. polyacrylonitrile, polystyrene, polycarbonate, polymethacrylate, combinations thereof, or the like, or other material which absorbs in the infrared or can be made to do so with infrared absorbing dyes. For the most part the particle composition without the dye will not absorb significantly in the infrared region of interest, usually absorbing less than about 25% of the total light absorbed in that region compare to the particle doped with the infrared absorbing dye. Also, there will be many regions in the visual region in which the particle composition will be substantially transparent, as distinguished from carbon or colloid particles which do not transmit light over the visual and infrared region. Usually, at least 50 weight %, preferably at least about 75 weight %, will be of a size or diameter within the range indicated.

The particles may be modified in a variety of ways. The particles may be chemically activated by having functional groups present on the surface of the particles, or be coated with a compound, e.g. protein, which may serve to substantially irreversibly (under the conditions of the processing and assay) bind to the dye. The coating compound may be the binding component, which will be involved in the aggregation of the particles, or other compound, usually being a protein. Alternatively, depending on the nature of the particles, the particles may not have chemically active groups, but rather provide binding by adsorption. In addition, infrared absorbing dyes which are stable under the conditions of formation of the particles, e.g. extrusion, may be mixed with the polymer prior to particle formation and the particle formed with the dye distributed throughout the particle.

A binding component is bound to the particle surface which provides for aggregation of the particles. The aggregation may be a result of the interaction of the binding component with the same or a different component on another particle or with an agent in the medium, which agent may be the compound of interest, a member of a specific binding pair, or a catalytic agent, e.g. an enzyme, which interacts, usually reacts, with the binding component to modify the binding component to cause aggregation. The specific binding pair will usually consist of the binding component and the component of interest, a reagent which competes with the component of interest for binding to the binding component, or a reagent which binds to the component of interest. These may be illustrated by: an antigen and antibodies to the antigen as the binding component; a dimer of the component of interest binding to Fab as the binding component; and fibrinogen and thrombin. The binding component bound to the surface will vary widely as to its nature, depending upon the component of interest and the protocol which is employed.

The binding component may be a small molecule, as small molecules were described previously, or a higher molecular weight molecule, or even in some instances, combinations such as virus or cell fragments or intact viruses or cells. Any of the compounds previously discussed may serve as the binding component. In one group of assays employing specific binding pairs for aggregation, where one is interested in binding to naturally occurring or synthetic components of interests, specific receptors may be employed, such as naturally occurring receptors, e.g. enzymes, lectins, surface membrane proteins, etc., or antibodies, either antisera or monoclonal antibodies. In other assays, one may employ one member of a naturally occurring specific binding pair, such as fibrin (prepared in the assay medium from fibrinogen), which can bind to various proteins. The use of fibrinogen in conjunction with the platelet protein GPIIb/IIIa will be discussed in greater detail subsequently. Various integrins may be used in conjunction with various adhesive proteins and vice versa. Antibodies may be assayed, where one could have the epitope which binds to the antibody bound to the particle. The epitope could be present as a small molecule, such as a synthetic organic molecule or an oligopeptide, or could be a polyepitopic molecule where one or more antibodies in the medium bind to the various epitopes of the antigen. Where the component of interest is monoepitopic, one may employ as a reagent a dimer or higher order of the monoepitopic compound, which reagent will serve to cross-link. Where nucleic acids are concerned, one may provide for oligonucleotides bound to the particles which bind to different sites on the strand of interest. Alternatively, one may prepare a strand which has repeats of the same sequence as a reagent which can compete with the nucleic acid component of interest, so as to cross-link the particles. Also, as indicated previously, one may use combinations of naturally occurring specific binding pairs, such as CD4 and gp120, P-selectin and L-selectin and their correlative homing receptors, CD3 and MHC, integrin adhesion receptors and their adhesive ligands, growth receptors and growth factors, cytokines and their cell surface receptors.

The particles are loaded with a dye which absorbs in the infrared. Various dyes have been reported as useful in this absorption range. See for example Fabian et al., Chem. Rev. (1992) 92:1197–1226. These dyes include bacteriochlorin, bacteriochlorophytin, meropolymethine dyes, benzoannulenes, vinylogous porphyrins, polymethine dyes, cyanines and merocyanines, and the like. The particular dye which is selected is one of convenience, availability, stability, compatibility with the particle, and the like. Specific dyes of interest include dyes of the class of pthalocyanines, napthalocyanines, metaled napthalocyanine dyes, and modified natural bacterochlorines. Specific example dyes include IR-140, 1,1'-Diethyl-4,4'-dicarbocyanine iodide, 1,1'-Diethyl-2,2'-quinotricarbocyanine iodide, Vanadyl 3,10,17,24-tetra-tert-butyl-1, 8, 15, 22-tetrakis(dimethylamino)-29H,31H-phthalocyanine, IRA800 (from Exciton), ProJet 830NP (from Zeneca). These dyes may be incorporated directly into the particle itself, through polymerization or passive adsorption. Alternatively, the dyes may be linked to the bead in combination with the binding component, such that they do not leach from the surface. The dyes will absorb light in the range of about 750–900 nm, particularly in the range of about 750–850 nm. For samples with high levels of red blood cells, the light will be at about 800 nm±10 nm, which is the isobestic point for oxyhemoglobin and reduced hemoglobin. The amount of the dye employed with the particles will vary with the extinction coefficient of the dye in the light range of interest, the required sensitivity of the assay, the size of the particles, the mode of binding of the dye to the particles, compatibility of the dye with the particle matrix, and the like. Usually, loading will be in the range of about 1 to 20 weight percent, more usually 5 to 15 weight percent.

As already alluded to, other reagents may be present. Particularly, where a monoepitopic compound is the component of interest. With a monoepitopic compound, where specific binding pairs are involved for cross-linking, in order to get cross-linking, one will need at least a dimer of such component or a mimetic analog thereof. Usually the reagent will have not more than about 5 of the cross-linking epitopes present. With this polyepitopic reagent, in the absence of the component of interest, there will be aggregation. Increasing amounts of the component of interest will reduce the amount and rate of aggregation. Alternatively, one may use multi-binding receptors which will crossreact with the binding component and the component of interest. The component of interest will fill the binding sites of the receptors, preventing crosslinking, again reducing the amount and rate of aggregation. In this way, one can detect monoepitopic compounds.

One may assay compounds which activate or inhibit catalysts, whether naturally occurring or synthetic, particularly enzymes which can activate the binding component to cause aggregation, e.g. thrombin and fibrinogen, casein or fibronectin and transamidases, etc.

Other reagents which may be present include substances which may modify the component of interest, such as activating a particular cellular function, upregulating or downregulating expression of a particular surface membrane protein, competing with the component of interest for the binding component on the particle, blocking binding by a substance which competes with the component of interest for binding to the binding component present on the particle, e.g. alleles, isotypes, etc., in order to avoid false positives associated with the competitive substance, and the like. These additional reagents will be selected in accordance with the nature of the component of interest, the protocol of the assay, and the like.

In each case the amount of the other reagents will be determined empirically. If one is using a polyepitopic reagent for competition with a monoepitopic component of interest, the reagent will be selected to give the highest sensitivity over the dynamic range of interest. This may vary from less to greater than stoichiometric and may be readily determined. One varies the concentration of the reagent with the lowest anticipated concentration of the component of interest and the highest anticipated concentration of the component of interest. One may the choose one or two intermediate points to determine the greatest sensitivity at these intermediate points. By graphing the results, one can determine the concentration of the reagent which will provide the most sensitive result over the dynamic range, a higher response being required at the lower part of the range than at the higher part of the range.

In carrying out the subject method, the sample, which may have been subject to prior preparation, is combined with the necessary reagents with mild agitation. Various conventional procedures for preparation of the sample may be employed. Depending upon the nature of the sample, the sample may be protected from the atmosphere or be in contact with the atmosphere. Protection from the atmosphere may be achieved by employing sealed containers, where the containers are sealed with a septum, and the sample is introduced by means of a needle through the septum, with the receiving container being evacuated or containing an inert gas.

Conveniently, relatively large or small samples may be taken and only small aliquots used in the assays. Thus, the assay volume may be from about 5 $\mu$l to 500 $\mu$l, usually from about 25 $\mu$l to 250 $\mu$l, and conveniently from about 25 $\mu$l to 150 $\mu$l.

The sample is combined with the particles and any other reagents under conditions where the particles are rapidly dispersed throughout the sample. The particles and other reagents may be present as a dry composition or dispersed with a small amount of liquid. Usually the volume of the particles and reagents will be not more than about an equal volume to the sample, preferably less than about 50% of the sample volume, more preferably less than about 25% of the volume sample.

A reading is taken at 0 time or some convenient interval to obtain a 0 value, which is the value in the absence of significant aggregation. Readings may then be taken from time to time. Automated instrumentation can be employed to mix the sample with the particles and any other reagents, heat the assay mixture to the desired temperature, carry out any necessary operations during the assay, monitor the assay mixture to take the first reading, for example, when the sample has reached the desired temperature, take additional readings, as appropriate, and then calculate the assay result for the sample, with any other descriptive information associated with the sample.

The concentration of particles in the medium will be optimized in accordance with the nature of the component of interest, the dynamic range of the component of interest, the nature of the sample medium, and the like. The amount of the particles may be determined empirically. Generally, the aggregation media absorption coefficient should be at least twice the absorption coefficient of the sample, preferably at least three times, more preferably at least about four times, and may be ten times or more. In the absence of any substantial background in the infrared, there is no effective ratio.

The time for mixing may be varied widely, usually being at least about 1 sec. and not more than about 5 min., usually not more than about 2 min., and preferably for about 5 sec. to 1 min. The particular manner of agitation is not critical to this invention, so long as it provides for thorough mixing, without preventing the formation of aggregates. If desired, mild agitation may be maintained during the course of the assay, again insuring that there is homogenous distribution of the particles and any other particulate matter, while insuring that aggregation is not impeded.

The temperature for the assay may be varied widely, depending upon the nature of the component of interest. Conveniently, ambient temperatures may be employed, although elevated temperatures which can be controlled and maintained are preferred. Where nucleic acids are involved, the temperature may be elevated, so as to enhance the degree of stringency of hybridization. Thus, the temperature may vary from about 15–90° C., where with other than nucleic acids, the temperature will generally vary from about 25–40° C. Usually, with nucleic acids the temperature will generally be in the range from about 20–90° C., more usually in the range of about 30–85° C.

With nucleic acids, stringencies may be achieved by using salts, organic solvents, and the like. However, with other than nucleic acids, normally the only addition will be a buffer, if at all, where the buffer will range from about 5–10 in pH, more usually from about 6–9, and at a concentration of from about 10–500 mM, more usually from about 25–250 mM.

The time for the assay will vary depending upon the manner in which the measurement is taken. Where zero time is carefully controlled, one may take one or two measurements at different time intervals to determine the absolute infrared transmission at the time intervals or determine the rate of formation of the aggregation. Alternatively, one may take a plurality of measurements over the time course of the assay and analyze the slope beginning at a fixed time from the time of mixing. The data may be analyzed by any convenient means, particularly using an algorithm which can manipulate the data in relation to calibrators and/or controls. The total time of the readings from the zero time (time of mixing), may range from about 10 sec. to 5 min., more usually about 30 sec. to 5 min., and preferably about 30 sec. to 2 min.

Usually, the result will be compared to a calibrator, which may be performed concomitantly or have been performed previously or may be provided as a standard curve. The calibrators will vary depending upon the nature of the component of interest. Samples having known amounts of the component of interest may be prepared and performed in the assay and the results charted so as to be able to translate the measurement obtained with the sample to the standard. In some instances controls will be used, where the base value may vary depending on the source of the sample. The particular control will be associated with the sample and the component of interest.

The subject invention finds particular application in conjunction with the determination of platelets and platelet function. Platelet adhesive function is an extreme test of the subject methodology in the sensitivity to various factors of platelets. First, platelets can be activated to varying degrees by the physical manipulation of blood and by the release of factors elicited when blood vessels are damaged on venipuncture. Second, is the effect of the time between drawing the blood and testing: for techniques requiring plasma this time is necessarily longer and therefore less desirable. In addition, the mechanical action needed to separate plasma from red cells can activate the platelets to varying degrees and also result in variable cell recovery. When measuring the effectiveness of inhibitors of platelet adhesive function, there is the issue of the relatively fast off-rate. The rapid off-rate of an inhibitor means that its effect will be underestimated if the sample is diluted prior to assay, and in some cases, even if the dilution occurs during the assay. Also, since platelet aggregation, fibrinogen binding and, in some cases, inhibitor binding are calcium dependent, the choice of anticoagulant may be important in accurately determining platelet function levels. Variability in absorption, metabolism, etc., of the anti-IIb/IIIa drugs may lead to large differences in pharmacokinetics. The subject methodology allows for a rapid determination of the effective level of inhibition of platelet adhesive function and/or the ability of platelets to aggregate. This information, permits accurate decision making on timing and frequency of dosing with anti-platelet drugs aimed at inhibiting clot formation.

Where platelet aggregation is to be measured, because of interest in the platelet status of an individual, which may be the natural status or the status resulting from administration of a drug, the sample will be in effect whole blood, which has been subjected to less than about 50%, preferably less than about 20% dilution.

The whole blood is drawn desirably in the substantial absence of air. Conveniently, a Vacutainer is employed for capturing and holding the blood sample. The Vacutainer desirably includes a small volume of a solution of sodium citrate generally in the range of about 3–5% sodium citrate having a volume in the range of about 0.05–0.5 ml. The blood sample should be obtained from an extremity free of peripheral venous infusions. Conveniently, the needle should be at least about 21 gauge.

The first tube which is withdrawn is discarded, the second tube or subsequent tubes being used. Mild agitation, simply gently inverting the Vacutainer is employed to insure the mixture of the anticoagulant with the sample. The sample in each container may range from about 1–10 ml, more usually from about 1–8 ml, conveniently from about 1–5 ml. The sample should not be stored for an unduly long period, generally storage before the assay should not exceed 1 hour.

A small portion of the sample may now be transferred to a cuvette for measurement. Generally, the volume may range from about 25–500 μl more usually from about 75–250 μl. Conveniently the cuvette contains the particles which have been coated with fibrinogen. The platelets may be activated by the addition of various agents, which serve to activate the platelets. Illustrative agents include iso-TRAP (See U.S. Pat. No. 5,455,228), TRAP, ADP, collagen, thrombin, ristocetin, or any combination thereof. Any convenient activator may be employed. Iso-TRAP is employed at a concentration in the range of about 1 to 5, preferably about 2 μmol/L. The activating agent may be incorporated with the bead reagent to which the blood sample is added. The beads and other reagents may be dry, so as to not dilute the sample, although in some instances a small amount of liquid may be present, desirably less than about 25% of the volume of the sample.

The particles are conveniently polystyrene particles of a size in the range of about 2 to 8 microns, which have been coated with fibrinogen by passive adsorption or by covalent linkage in accordance with conventional ways. Generally, the weight of fibrinogen to the weight of particles will be in the range of about 1:1000 to 1:10.

The amount of beads should provide a ratio between the agglutination media absorption coefficient and whole blood absorption coefficient of greater than about 4:1 at 800 nm, generally not more than about 10:1 at 800 nm. The optimal absorption ratio may be achieved by configuring both the light-absorbing characteristics of the agglutination media and the concentration of the agglutination media in the assay sample.

The mixture of citrated whole blood, particles and activating agent is gently agitated to insure homogeneity and the mild agitation is continued so as to maintain homogeneity without impeding aggregation formation. The temperature for the medium will be maintained at a constant temperature. After a short time, generally under 30 sec., usually under about 10 sec., readings are begun by illuminating the sample with light at about 800 nm. The total time for the readings will generally be under about 5 min, usually under 3 min, where, when one is determining the rate of change to determine the change in slope with time, the number of data points per second may range from about 0.01 to 100, more usually from about 1 to 50. Thus one may take readings at constant intervals of from about 0.01 sec to about 1.5 sec, usually from about 0.02 sec to 1 sec. Otherwise, data points may be taken as convenient, there being at least one data point, more usually at least two data points, frequently not fewer than 1 per minute. The change in transmissibility with time is determined by any convenient technique, conveniently employing a conventional spectrophotometric detector for the infrared.

As a control, blood containing a coagulation inhibitor is treated with a reagent, conveniently an antibody or fragment thereof which completely neutralizes the inhibitor. It is found that the baseline for platelet activity can vary widely with time for a patient and between patients, so that by neutralizing the inhibitor one can get the baseline value for platelet activity for the particular sample. This may then be used for comparison with the results obtained with the sample to determine the platelet activity in the presence of the inhibitor. Illustrative compounds which find use as coagulation inhibitors include Searle compounds 54701B and 57101A, which are potent IIb/IIIa function blocking drugs. Antisera or monoclonal antibodies or binding fragments thereof can be used to block the action of the inhibitor and the resulting uninhibited sample used for the control. The control would be used in the same way as the sample and could be run concurrently so that the same conditions are employed for the control as are employed for the sample.

The amount of inhibitor neutralizing agent which is employed will provide for complete neutralization of the inhibitor and excesses may be used, usually not more than about five-fold excess of the maximum concentration of the inhibitor, as anticipated from the dose given to the patient, without significant dilution of the sample, usually less than about 50% dilution, usually less than about 25% dilution. Where antiserum or fragment thereof is used, high affinity titers should be used, desirably 50% maximum binding should be at a titer ranging from at least about 1:10,000 and maybe 1:100,000 or more, preferably at least about 1:25,000. By employing this technique, one may establish a baseline rate, or any other IIb/IIIa functional test baseline parameter.

As a calibrator, the subject particles without fibrinogen, serving as surrogate platelets, can be combined with thrombin in an appropriate buffered medium. This reagent may then be combined with the particles coated with fibrinogen in the same manner as the sample. If desired, the buffered medium may be augmented with blood constituents, such as red blood cells, serum albumin, immunoglobulins, or other significant constituent of blood, which does not participate in the aggregation of the particles. A convenient buffer medium Is a HEPES-sodium chloride buffer comprising from 1–5 mg/ml protein e.g. BSA.

If one wishes, this technique as modified may also be used in evaluating the activity of various proteins in the blood, which are associated with thrombin activation and aggregation. These proteins include FV, FVIIIc, FIX, and other factors previously described. Thus, by adding a blood sample to a prepared mixture, which may be dry and require reconstitution or a concentrated solution, which contains the necessary blood factors for coagulation, except for the factor to be measured, and the fibrinogen coated particles, a change in the rate of aggregation will be related to the activity of the factor of interest in the sample. The result may then be related to calibrators having known amounts of the factor of interest.

After the sample has been combined with the reagents, desirably it will be heated to a temperature above room temperature, but below interference with the assay, so as to insure that the temperature can be controlled without adversely affecting the assay result. Desirably, the temperature should be at least 25°, preferably in the range of 30–40°, more preferably about 37° C. While not essential, it is preferable that the sample be mildly agitated during the incubation and measurement of the aggregation. For agitation, metal beads may be moved up and down, magnetic beads oscillated at a slow rate or other means employed for mild agitation.

The sample volume can be quite small, usually being not less than about 10 $\mu$l, more usually not less than about 25 $\mu$l, and desirably not more than about 1 ml, preferably not more than about 500 $\mu$l, more preferably not more than about 250 $\mu$l.

For convenience, kits can be provided comprising some or all of the reagents which find use in the subject invention. The kit will have the particles for use with the component of interest. In addition, neutralizing immunoglobulins may be provided for removing inhibitor in a sample to serve as a control. Calibrators may be provided providing particles with the appropriate binding component mixed with any other reagents associated with the assay and, if desired, a source of the component of interest, either in measured amounts or in bulk. For platelet aggregation, a combination of thrombin and uncoated particles may be supplied. Also, of convenience, would be Vacutainers comprising 0.1–1 ml of 1–5M anticoagulant, e.g. sodium citrate. Of particular interest for the kit is a container containing one or more of the appropriate reagents in order to reduce the manipulative steps for the assay. For example, a container, such as a cuvette, may be provided containing the particles and, as appropriate, other reagents for the assay.

The following examples are offered by way of illustration and not by way of limitation.

EXPERIMENTAL

The beads used in the subsequent experiments were prepared as follows:

Preparation of human fibrinogen-coated latex beads

To 8.369 mL of DI water in a 15 mL polypropylene conical tube is added 0.208 mL of 0.96M sodium phosphate at pH 7.2 with 0.02% sodium azide. Four hundred and twenty-three microliters of human fibrinogen (from Enzyme Research Laboratories, South Bend, Ind.; cat # Fib 3) at 7.8 mg/mL is then added and gently mixed. Finally, 1 mL of 5.5 micron latex beads (from Bangs Laboratories; polystyrene with 5.5% DVB and 5% methacrylic acid) at 10% is added and the mixture is incubated at room temperature on a rocker for 2 hours. It is then centrifuged at 1540 g for 5 minutes on a swinging bucket rotor. The supernatant is decanted and 10 mL of Buffer A (10 mM HEPES with 1 mg/mL BSA and 0.02% sodium azide at pH 7.5) is added to resuspend the beads. The mixture is centrifuged and the above procedure carried out again. After the last centrifugation, the supernatant is decanted and 6.67 mL of Buffer A is added to resuspend the beads. The bead concentration is usually $1.38 \times 10^8$ beads per mL. A modification of the bicinborinic acid (BCA) assay (Pierce, Rockford, Ill.) is used to determine the amount of fibrinogen coated on beads. The preparation of human fibrinogen-coated blue latex beads is done in an identical fashion, except that 6 micron blue latex beads (from PolySciences, polystyrene with carboxylate groups) are used.

Preparation of IR-140 Dye Solution

Forty-five milligrams of IR-140 is dissolved in 9 mL of methylene chloride in a glass tube. It is then mixed with 38 mL of 2-propanol, followed by 53 mL of Buffer B (20 mM sodium phosphate with 0.02% sodium azide at pH 7.5) in a glass jar. The mixture is mixed vigorously with a Cole-Palmer stirrer Model 50002-30 for 15 minutes to make a homogeneous dye solution.

Preparation of IR-140-dyed human fibrinogen-coated latex beads

To a pellet of human fibrinogen-coated latex beads ($1 \times 10^9$ beads) is added 10 mL of the above IR140 dye solution, followed by vortexing. The mixture is incubated at RT on rocker for 5 minutes and then transferred to a 50 mL polypropylene conical tube and QS'd to 50 mL with Buffer A. After 5 min of spin at 1540 g and removal of supernatant, the above dye-loading process is carried out a second time. After centrifugation and removal of supernatant, 9.75 mL of Buffer B is added and vortexed, followed by addition of 0.25 mL of 7.8 mg/mL human fibrinogen and gentle mixing. The mixture is then sonicated for 45 seconds. Purification (use of Buffer A and centrifugation) is carried out the same way as in the Section on Preparation of human fibrinogen-coated latex beads.

In the following experiment, the subject methodology was employed in conjunction with the Searle compound 54701B, a compound having platelet aggregation inhibition capability. The method employed was as follows.

General Approach

Citrated blood is added to a cartridge containing proprietary microparticles and thrombin receptor activating peptide (iso-TRAP). Microagglutination is optically monitored as the mixture is mechanically mixed. Platelet activity is determined by the rate of change of the optical density of the solution. The results of this assay are compared to results from optical platelet aggregometry performed on platelet rich plasma (PRP).

Methods

Specimen Collection and Preparation

Human blood (40.5 ml) was collected from six non-smoking aspirin free volunteers into 5.0 ml citrated (3.8%) tubes using a Vacutainer system (Becton Dickinson, Franklin Lakes, N.J.) with a 21 gauge needle. The first tube was discarded and the remainder pooled into a polypropylene container and maintained at a room temperature. Aliquots of 5 ml of pooled blood were transferred to 12×75 mm polyproplyene tubes and 250 µl of blood withdrawn and discarded. Searle compound 54701B was diluted with 10 mM HEPES, 150 mM NaCl, pH 7.4 and 50 µl added to each tube resulting in final concentrations of 10, 25, 35, 50 and 75 nM. A minimal aggregation sample at 1000 nM was prepared for all samples. Control samples to assess maximum aggregation were prepared simultaneously with 250 µl of the HEPES/Saline buffer added in place of the antagonist.

Aliquots of whole blood with inhibitor (2.0 ml) were removed and placed into separate polyproplyene tubes for performance of the Rapid Platelet Function Assay (RPFA). The remainder of the blood in the tubes was centrifuged at 110×G for 12 minutes and the platelet-rich plasma (PRP) collected into separate polypropylene tubes. Platelet poor plasma (PPP) was prepared by centrifuging a separate aliquot of blood at 1540×G for 15 minutes. Assays for platelet function were begun within 1 hour of blood collection.

In a similar study depicted in FIG. 4, blood was collected and treated as above, except that six donors were drawn on three consecutive days. Hence, the results are reported as an average of the data obtained on those three days.

Platelet Aggregometry

PRP (400 µl) was pipetted into a siliconized cuvette containing a Teflon coated stir bar. The cuvette was placed into a Chrono-Log model 490D optical platelet aggregometer and a baseline tracing was established for 30 seconds. ADP (44 µl) at 200 µM was added for a final ADP concentration of 20 µM. Aggregation was monitored for two minutes and the maximal aggregation recorded.

Rapid Platelet Function Assay

A 160 µl aliquot of the whole blood with inhibitor or buffer prepared above for the RPFA was added to a plastic cuvette containing lyophilized iso-TRAP and microparticles. The mechanical mixing cycle was activated for 70 seconds with optical reading sampled at a rate of 16 per second. Microagglutination was determined by the rate of change of the optical density of the solution over a fixed interval.

The RPFA monitor uses an IR diode with peak wavelength at 805 nm, a spectral bandwidth of 50 nm, and a radiant output power of 15 mW. The transmitted signal is detected by a high gain wide-bandwith optical detector amplifier hybrid with a responsivity at 805 nm of 0.6 A/W. Upon addition of the 160 µL whole blood sample to the assay cartridge, a motor driven mixer is run for a duration of 70 seconds at 240 cycles/min. During this mixing period, the detector signal output is sampled at a rate of 16 Hz. Upon completion of mixing, the raw time domain data is processed to provide a measure of platelet inhibition.

Results

As can be seen in FIG. 1, the rate of agglutination of the 6 micron fibrinogen-coated blue latex beads as monitored in a system employing a LED light source at around 650 nm showed almost a two fold increase upon total oxygenation of the dark venous whole blood, whereas that of the 5.5 micron IR-140-dyed fibrinogen-coated latex beads as monitored in a system employing a LED light source at around 817 nm stayed constant.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for determining platelet binding function in a sample, employing an agglutinating system comprising particles to which fibrinogen is bound, which particles comprise an infrared light absorbing dye, said method comprising:

combining a blood sample comprising platelets with said agglutinating system to form an assay mixture;

irradiating said assay mixture with light having a selected infrared region wavelength known to be absorbed by said dye, wherein a level of said infrared light of said wavelength is transmitted through said assay mixture;

determining the level of transmission of said infrared light of said wavelength through said assay mixture;

wherein said level of transmission or a change in said level of transmission over time is an indication of binding function of said platelets in said sample for said particle bound fibrinogen.

2. The method according to claim 1, wherein said agglutinating system comprises a platelet activating compound.

3. The method according to claim 1, wherein said blood sample is diluted less than about 5 fold in said assay mixture.

4. The method according to claim 3, wherein the wavelength is about 800 nm.

5. The method according to claim 1, wherein said particles are of a diameter in the range of 1 to 10 $\mu$m.

6. The method according to claim 5, wherein said diameter is in the range of 2 to 8 $\mu$m.

7. The method according to claim 1, comprising the additional steps for determining a calibration value of:

combining a mixture of thrombin and uncoated particles with said agglutinating system in a calibration mixture, wherein said particles having bound fibrinogen and said uncoated particles have comparable concentrations in said calibration mixture, whereby agglutination of said fibrinogen-bound particles occurs;

irradiating said calibration mixture with said light having said infrared region wavelength, wherein a level of said infrared light of said wavelength is transmitted through said calibration mixture; and determining the level of transmission of said infrared light of said wavelength through said calibration mixture;

wherein the level of transmission or a change in said level of transmission over time is indicative of the calibration value without participation of platelets.

* * * * *